(12) United States Patent
Engstrom

(10) Patent No.: US 7,914,508 B2
(45) Date of Patent: Mar. 29, 2011

(54) APPARATUS FOR REDUCING FAT CONTENT OF BLOOD

(75) Inventor: Gunnar K. Engstrom, Hörnefors (SE)

(73) Assignee: ESTR Engstrom Scientific and Technical Research Aktiebolag, Hörnefors (SE)

( * ) Notice: Subject to any disclaimer, the term of this patent is extended or adjusted under 35 U.S.C. 154(b) by 369 days.

(21) Appl. No.: 10/503,603

(22) PCT Filed: Feb. 3, 2003

(86) PCT No.: PCT/SE03/00178
§ 371 (c)(1),
(2), (4) Date: Feb. 7, 2005

(87) PCT Pub. No.: WO03/066136
PCT Pub. Date: Aug. 14, 2003

(65) Prior Publication Data
US 2005/0131333 A1   Jun. 16, 2005

(30) Foreign Application Priority Data
Feb. 8, 2002   (SE) .................................... 0200381

(51) Int. Cl.
*A61B 19/00* (2006.01)
*A61M 37/00* (2006.01)
(52) U.S. Cl. .................. 604/410; 604/408; 604/6.15
(58) Field of Classification Search .............. 604/4.01, 604/6.09, 408, 410, 6.15; 210/645, 348, 210/435, 513, 500.21, 532.1
See application file for complete search history.

(56) References Cited

U.S. PATENT DOCUMENTS

| | | | | |
|---|---|---|---|---|
| 3,866,608 A | * | 2/1975 | Reynolds et al. | 604/319 |
| 4,775,482 A | * | 10/1988 | Thurman | 210/668 |
| 4,994,022 A | * | 2/1991 | Steffler et al. | 604/7 |
| 5,049,146 A | * | 9/1991 | Bringham et al. | 604/6.09 |
| 5,133,703 A | * | 7/1992 | Boehringer et al. | 604/317 |
| 5,318,556 A | * | 6/1994 | Avallone et al. | 604/410 |
| 5,362,406 A | | 11/1994 | Gsell et al. | |
| 5,540,836 A | | 7/1996 | Coyne | |
| 5,573,526 A | * | 11/1996 | Hess | 604/408 |
| 5,827,243 A | * | 10/1998 | Palestrant | 604/524 |
| 6,264,890 B1 | | 7/2001 | Boehringer et al. | |
| 6,773,426 B2 | * | 8/2004 | Tamari | 604/406 |
| 2002/0156412 A1 | | 10/2002 | Rugenstein | |

FOREIGN PATENT DOCUMENTS

| | | |
|---|---|---|
| EP | 0 743 071 A3 | 11/1996 |
| EP | 0 771 570 A1 | 5/1997 |
| SU | 1504219 A1 | 8/1989 |
| WO | WO-92/10219 A1 | 6/1992 |
| WO | WO-02/38202 A1 | 5/2002 |

* cited by examiner

*Primary Examiner* — Leslie R Deak
(74) *Attorney, Agent, or Firm* — Birch, Stewart, Kolasch & Birch, LLP

(57) ABSTRACT

Apparatus for reducing the fat content of blood and in particular to an apparatus for reducing the fat content of pericardial suction blood has a conduit for blood, an absorbing filter located in the conduit and an associated temperature control device for adjusting the temperature of blood before it flows through the filter.

37 Claims, 14 Drawing Sheets

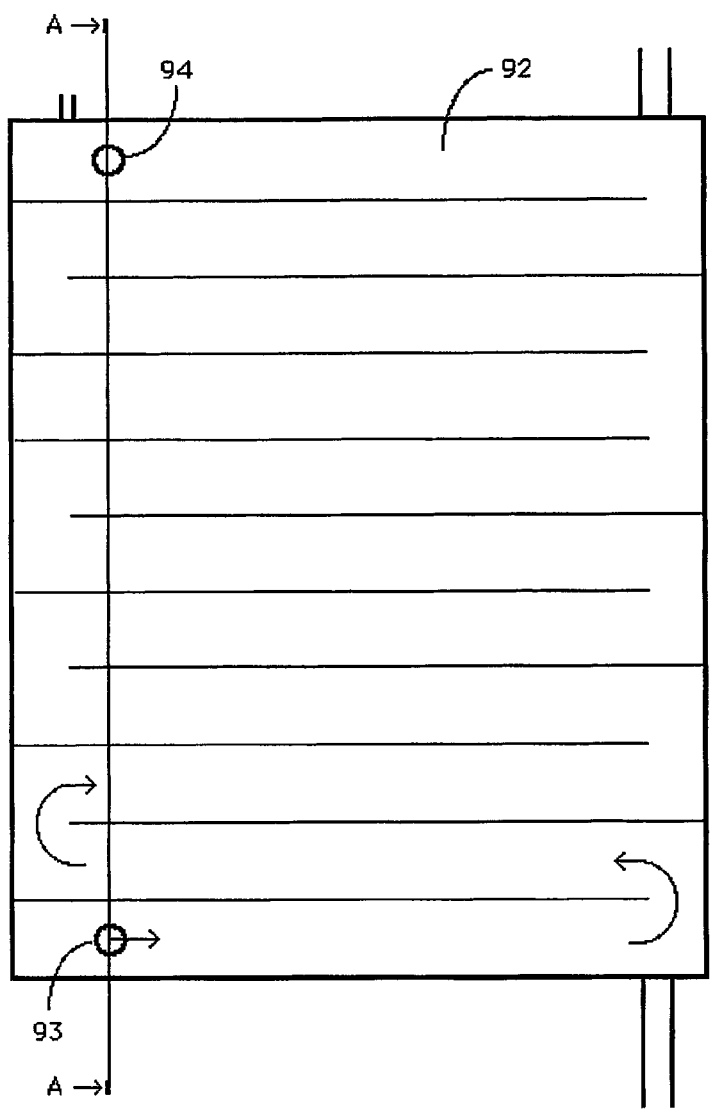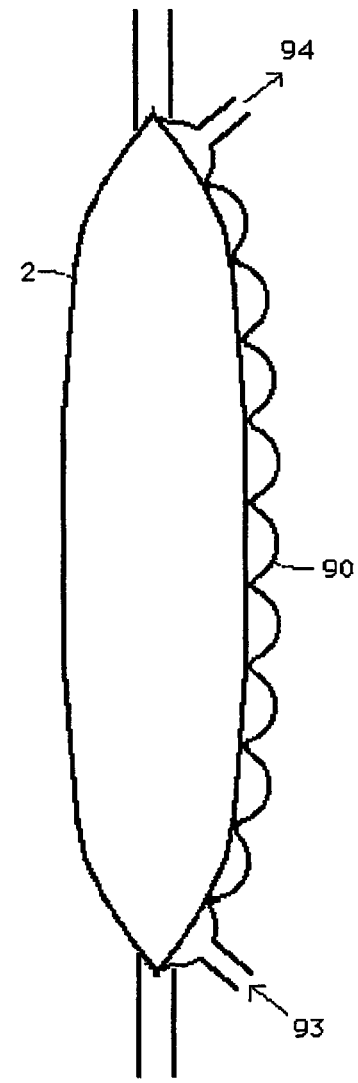
Figure 11                    Figure 12

APPARATUS FOR REDUCING FAT CONTENT OF BLOOD

BACKGROUND OF THE INVENTION

1. Field of the Invention

The present invention relates to an apparatus for reducing the fat content of blood and in particular to an apparatus for reducing the fat content of pericardial suction blood.

2. Description of background Art

Extra corporeal circuits are regularly used during surgery and in particular for open heart surgery and are controlled by a Perfusionist. Venous blood bypasses the heart in one such circuit and is reintroduced into an artery in a patient's body after it has been oxygenated. Pericardial blood is also removed from the surgical site and is combined with the venous blood, oxygenated and subsequently reintroduced into the patient's body. One of the remaining problems associated with cardiac surgery is post-operative neurological dysfunction. Cardiopulmonary bypass (CPB) operations have been linked with micro embolisms in the small arteries of the brain, known as SCADS. The embolic material found in the arteries is believed to contain liquid fat from the pericardial suction blood which is reintroduced into the patients body after collection.

A number of solutions have been proposed to overcome this problem. One such solution is to wash the pericardial suction blood, however this technique is relatively expensive and time consuming. Another solution is filtration, a technique that can be inefficient due to the difficulties associated with filtration of fat in liquid phase. A third solution is to avoid re-transfusion of the pericardial suction blood. This solution adds known problems associated with an increased use of allogeneic blood, such as immunological modulation.

SUMMARY OF THE INVENTION

It is an object of the present invention to overcome the problems associated with the above outlined solutions associated with removal of fat from pericardial blood by providing an efficient and relatively inexpensive technique for fat removal.

Accordingly, there is provided an apparatus for reducing fat in blood comprising a conduit for blood, an absorbing material of a filter located in the conduit and an associated temperature control means for adjusting the temperature of the blood before it makes contact with the absorber.

Preferably, the absorber comprises a porous structure, a mesh structure, or a fibrous mass structure of lipophilic material of variable depth that increases the contact surface area to blood, herein referred to as filter. The term filter may also comprise a thin structure of surface coating when so is described.

Ideally, the absorbing filter is in contact with blood, not necessarily meaning blood passing thorough the filter from one side to the other.

As the solid or high viscosity fat makes contact with, or passes through, the absorbing filter it adheres to the filter thereby reducing the fat content of the blood.

In another aspect of the invention, the temperature control means maintains the blood at a suitable temperature for transfusion back into the patient's body. At the maintained temperature, or slightly heated, the separation of fat from the blood medium may also be facilitated as the viscosity of fat is maintained or lowered.

Preferably, the temperature control means is provided by a heat exchanger in contact with the conduit.

Ideally, the absorber is manufactured from cellulose or polyester fiber but can also be based on derivatives of polyamides, polyolefins, or polyvinyl fluoride, although not being limited to any of these materials.

In another aspect of the invention, there is provided an apparatus for reducing fat in blood comprising a chamber having an inlet and an outlet wherein the chamber is arranged with a first compartment for receiving blood via the inlet and a second compartment in fluid communication with the first compartment via a channel which connects the base of the first compartments with the base of the second compartment, the second compartment defining the outlet, the compartments being dimensioned and spatially arranged relative to one another whereby in use blood flowing into the second compartment from the first compartment reaches the same vertical height as blood in the first compartment preventing the last portion of the blood in the first compartment flows out of the first compartment. Advantageously, the last portion of blood which has collected adjacent the top surface of the blood in the first chamber has a high concentration of fat which always remains in the first compartment.

Preferably, the channels are releasably sealable by sealing means.

Ideally, a blood pipe passes through the inlet, the chamber and the outlet and the portion of the blood pipe within the chamber defines perforations.

Preferably, a separate filter is located within at least one compartment.

Preferably, the heat exchanger is mounted on the chamber.

Ideally, the heat exchanger is provided by a heat exchange chamber having and inlet and an outlet.

In another embodiment, the heat exchanger is provided by a piezoelectric element.

Preferably, the apparatus can be supported on a holder.

Ideally, the holder is constructed from a light coloured material.

Preferably, the holder includes an illuminating background which makes the layer of fat easier to see.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will now be described with reference to the accompanying drawings which show by way of example only, nine embodiments of an apparatus for removing fat from blood. In the drawings:

FIG. 11 is an elevation view of a second embodiment of apparatus;

FIG. 12 is a side section elevation view of the apparatus of FIG. 11 taken along A-A;

DETAILED DESCRIPTION OF THE PREFERRED EMBODIMENTS

Figure 1:
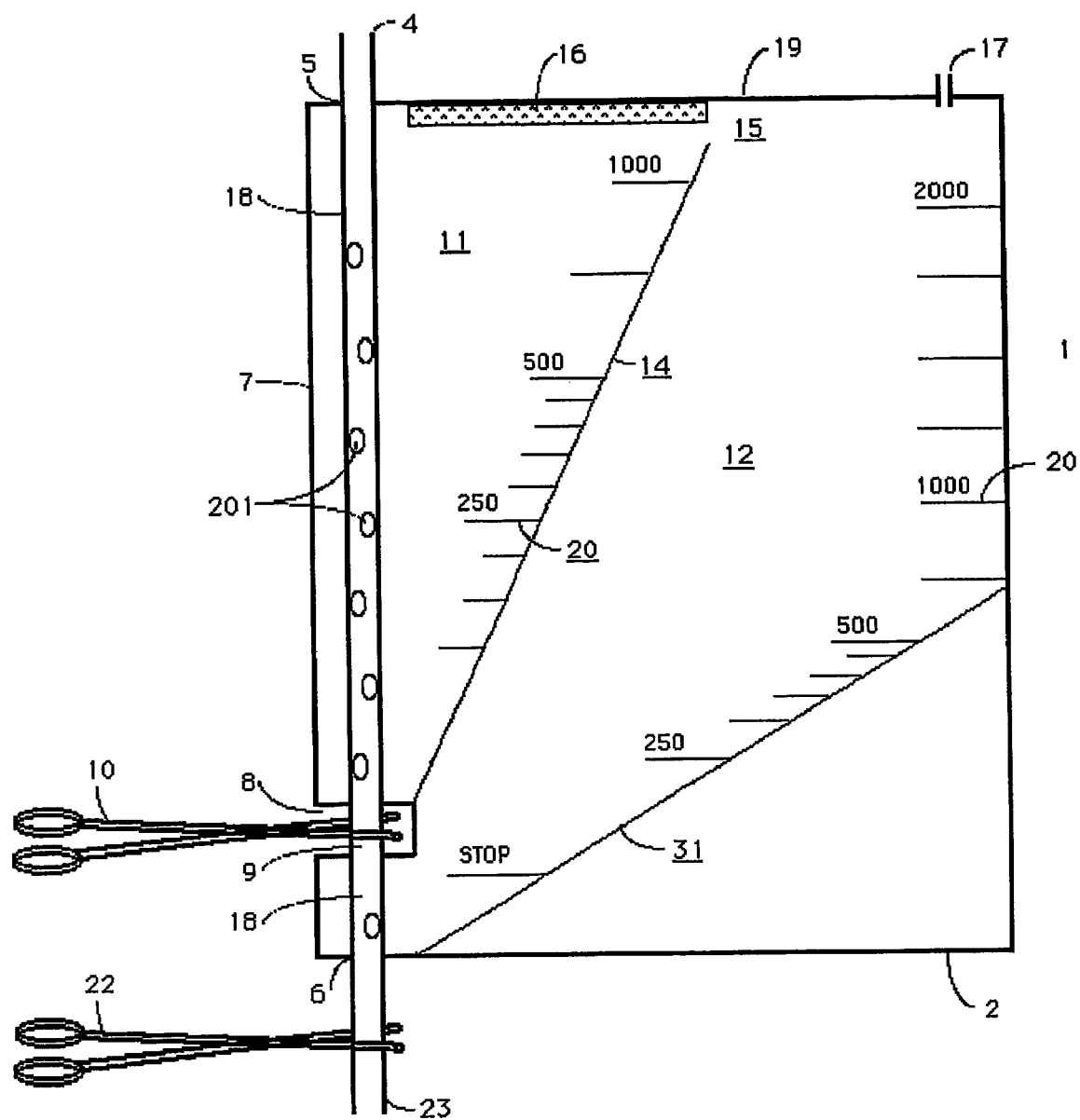
FIG. 1 is an elevation view of a chamber for separating fat from blood.

Referring to the drawings and initially to FIG. 1, there is shown a chamber 2 for separating fat from blood. The chamber 2 has an inlet 5 and an outlet 6. The chamber 2 has a substantially rectangular shape and a pipe 4 extends along one edge 7 of the chamber 2. The chamber 2 has a slot 8 on the edge 7 exposing a portion 9 of the pipe 4. The remaining portion 18 of the pipe 4 between the inlet 5 and the outlet 6 is enclosed within the chamber 2 and has perforations 201. The pipe 4 may be located anywhere within the chamber 2 with opening 8 exposing a portion of the pipe 4. A sealing clamp 10 is mounted on the exposed portion 9 of the pipe 4. The chamber 2 is divided into two compartments 11 and 12 by a welded seam 14. The compartments 11 and 12 are in communication via a first channel 15 due to an interruption in the seam 14 and a second channel, in this embodiment provided by the portion 9 of the pipe 4 bridging the slot 8. A de-foamer 16 and an air escape valve 17 are located along the uppermost edge 19 of the chamber 2 when the chamber 2 is in an in use position. A volume scale 20 for each of the compartments 11 and 12 is incorporated into the plastic material of the chamber 2. A second sealing clamp 22 is mounted on a portion 23 of the pipe 4 outside the chamber 2 after the outlet 6. The chamber 2 and pipe 4 described in this embodiment are produced from a pliable transparent plastic material, although they are not limited to this particular material. A chamber 2 manufactured from a rigid material is also within the scope of the invention.

In use, pericardial suction blood from a surgery site is pumped to the inlet 5 of the pipe 4 and continues down through the pipe 4 until it reaches the clamp 10. As blood abuts against the blocked pipe 4, barometric pressure forces blood and air from the wound out through perforations 201 in the portion 18 of the pipe 4. Blood collects in compartment 11 and the fat contained therein flows to the top of the blood under a normal process of separation. If the blood fills the compartment 11, it can flow over into compartment 12 via channel 15. The de-foamer 16 is activated in the event of foaming of blood in its vicinity. Seam 14 and an additional seam 31 promote the flow of blood towards the clamp 10 and the outlet 6 respectively when the chamber 2 is held in an in use position. When the perfusionist is satisfied that a substantial portion of the fat has collected in a layer on top of the blood in compartment 11, the clamp 10 is opened and under normal barometric pressure, the blood flows from compartment 11 into compartment 12. The geometry of compartments 11 and 12 and their spatial orientation relative to one another is designed so that a final volume of blood containing the layer of fat which has collected on top of the blood in compartment 11 remains in compartment 11 after the transfer of the blood to compartment 12. This design feature of the chamber 2 reduces the need for careful visual monitoring of the transfer of blood from compartment 11 to compartment 12 by a perfusionist, improving the functionality of the chamber 2. When substantially all of the blood from compartment 11 has transferred to compartment 12, the clamp 10 is reapplied to the exposed portion 9 of the pipe 4. It is not necessary, but it is possible, to stop the pump at any stage of the process. The compartment 11 refills with inflowing blood from the surgery site. The separated fat layer remains adjacent the surface of the blood. Fat contained in the blood flowing into the compartment 11 again begins to float towards the surface of the blood stored in the compartment 11. The fat contained in the blood stored in compartment 12 also floats towards the top surface. There is no turbulence from incoming blood to disturb the process of separation in compartment 12 so further separation of fat and blood occurs efficiently. The second clamp 22 is opened after a predetermined time and blood flows from the compartment 12 into a venous reservoir (not shown) or directly back to the body of a patient. The perfusionist prevents the last portion of the blood which contains the layer of fat from leaving compartment 12 through the outlet 6. The scale 20 on the chamber 2 is used for this purpose in conjunction with visual monitoring by the perfusionist.

This construction of chamber 2 provides the operator with a variety of uses for the chamber 2 when the chamber is manufactured from a pliable plastic material. On delivery, the chamber 2 is rolled around the pipe 4. If an operator wishes to avail of the function of fat separation, the chamber 2 is uncoiled from the pipe 4 and mounted on a holder (not shown). Alternatively, the chamber 2 can be manufactured having a short pipe 4 which is connected, or cut in, to an existing pipe used for standard and commercially available machinery of heart lung technology. These pipe-to-pipe connectors are of standard design and commercially available. The inlet pipe 5 and outlet pipe 6 may have branched connectors for in and out coming pipes. The chamber 2 includes a recess (not shown) in or about edge 19 for receiving a spike for releasably securing the chamber 2 on the holder. Alternatively, the chamber 2 can be used as a standard blood pipe 4 with the chamber 2 remaining wrapped around the pipe 4 during use. The air valve 17 is in a closed position on delivery and must be opened if the fat separation function is needed. If a large volume of blood is being removed from the surgery site, it is possible to use the chamber 2 in an open system, allowing blood to flow through the system continuously provided the inlet 5 and outlet 6 are in direct communication.

Figure 2:
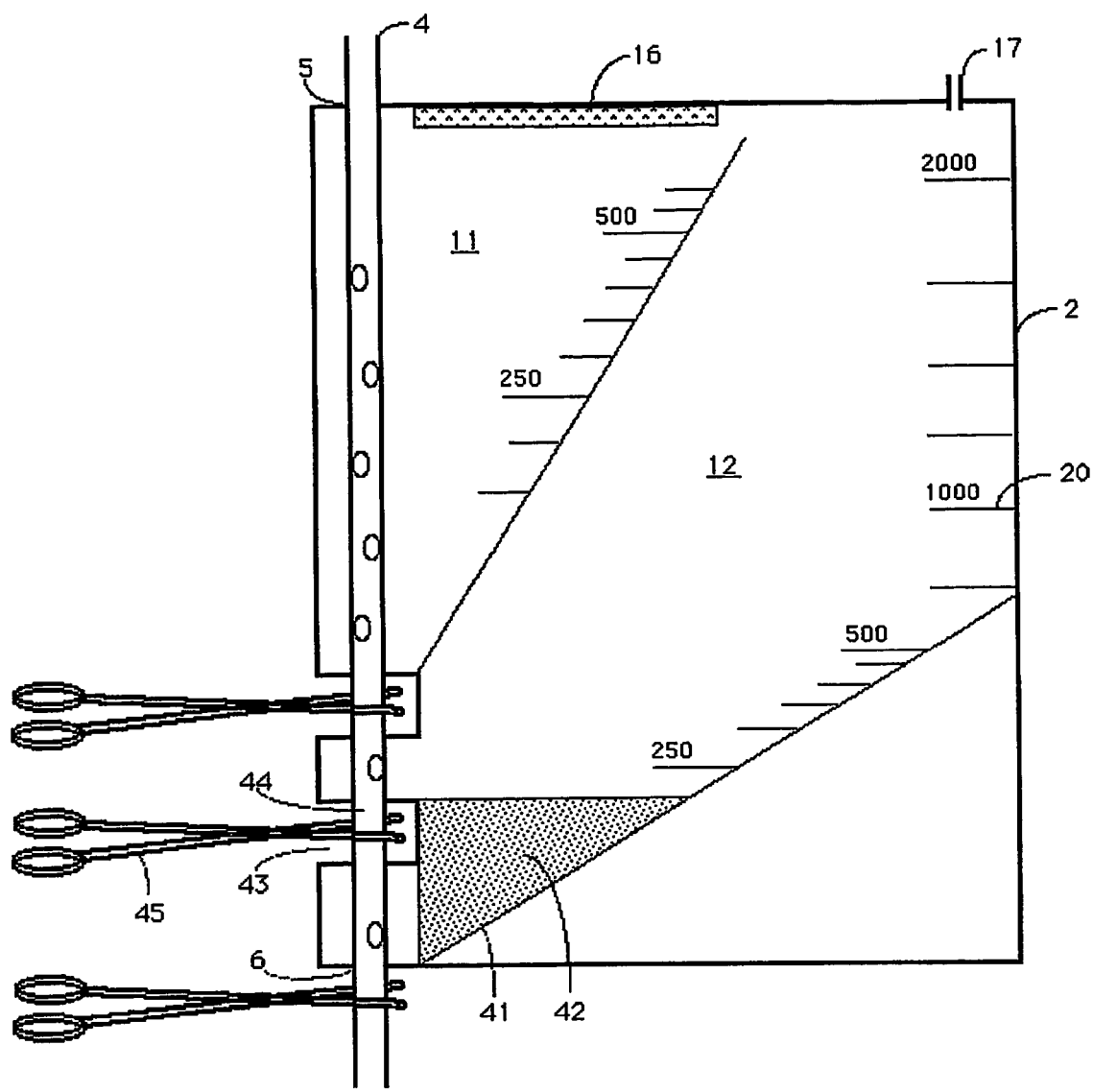
FIG. 2 is an elevation view of a second embodiment of chamber for separating fat from blood.

Referring to FIG. 2, there is shown a chamber 2 substantially as described in FIG. 1. Reference numerals used to designate features of the chamber 2 of FIG. 1 are used to designate identical features of the chamber 2 in FIGS. 2 to 6, which illustrate similar embodiments of the chamber 2. In FIG. 2, an additional compartment 41 is shown having an integral filter 42 welded or glued to the plastic material of the compartment 41. A second recess 43 exposes an additional portion 44 of the pipe 4 and a third clamp 45 is mounted on this portion 44. The chamber 2 works in the same way as the chamber 2 of FIG. 1 but including the additional step of blood in compartment 12 flowing into compartment 41 and contacting the absorbing material of the filter 42 prior to the blood flowing back to the venous reservoir or back into the patient's body. The filter 42 absorbs fat from the blood which has reached a partially solid state or fat which has an increased viscosity due to (1) cooling as a result of the blood being stored in the chamber 2 during the separation process and/or (2) cooling by a heat exchanger (not shown). This chamber 2 is also suitable for allowing through flow of blood by removing all the clamps 10, 22, 45, if high volume bleeding occurs at the surgery site.

Figures 3, 4:
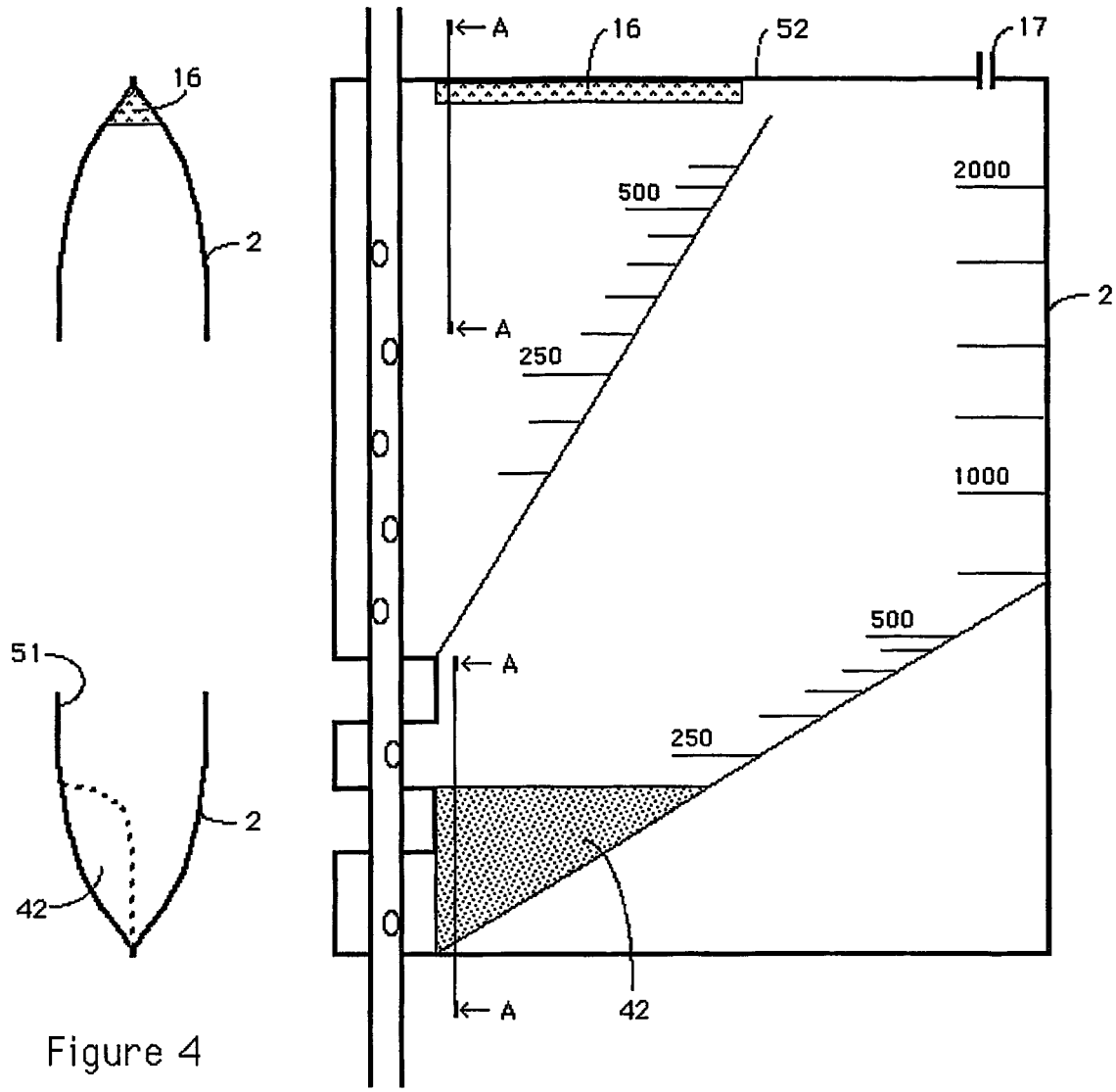
FIG. 3 is an elevation view of the chamber of FIG. 2.
FIG. 4 is a partial side section view of the chamber of FIG. 3 taken along A-A.
Figures 5, 6:
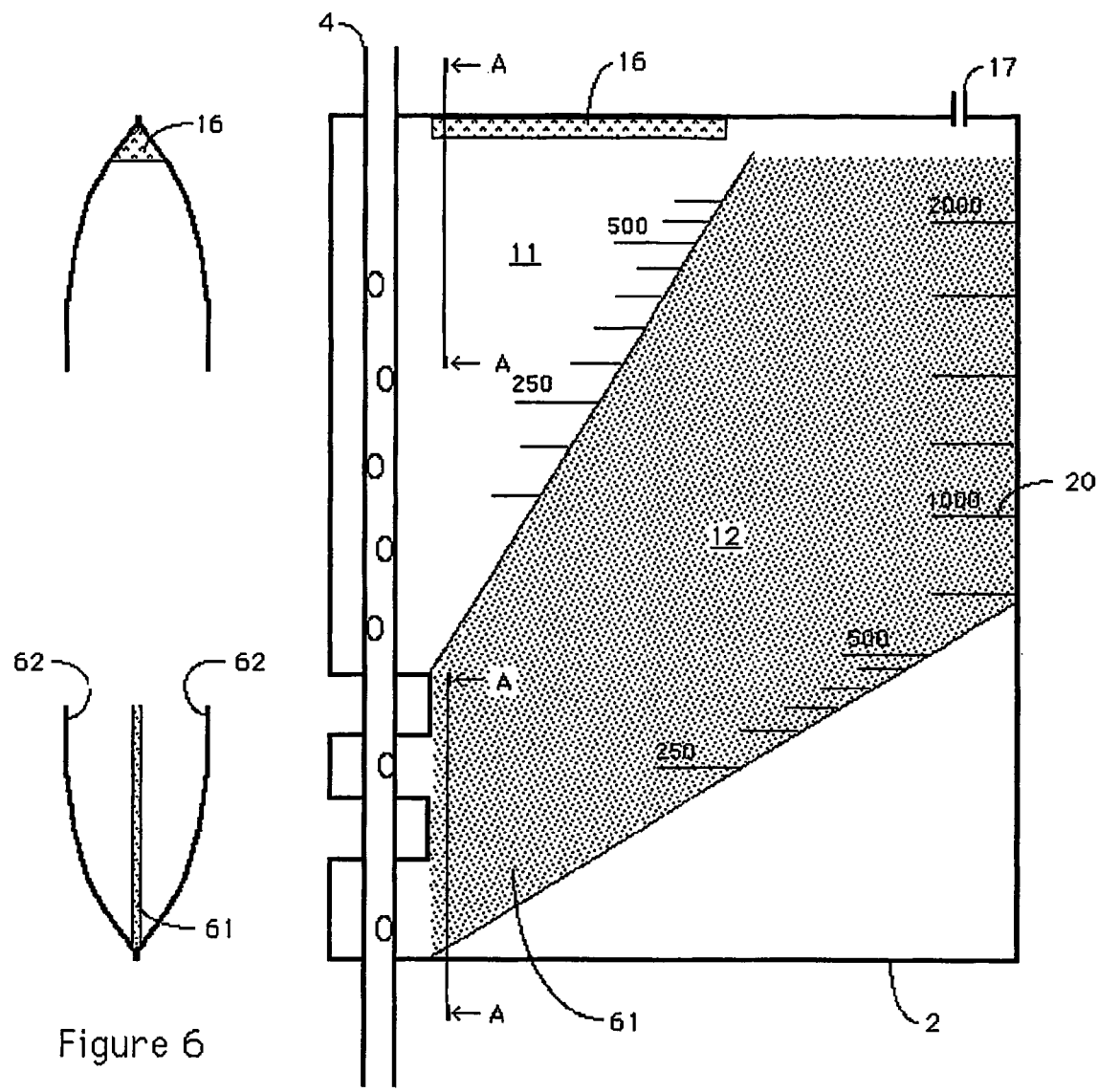
FIG. 5 is an elevation view of the chamber of FIG. 2.
FIG. 6 is a partial side section view of the chamber of FIG. 5 taken along A-A.

Referring now to FIG. 3 and FIG. 4, there is shown a chamber 2 as described in FIG. 2 above. FIG. 4 shows a filter 42 welded or glued to an internal surface 51 of the chamber 2. The de-foamer 16 is shown adjacent the top edge 52 of the chamber 2. Referring now to FIGS. 5 and 6, a second embodiment of filter 61 is shown which is free to move in the compartment 12 and without blood passing through the filter 61. Alternatively, the filter 61 can be fixed to either or both internal surfaces 62 of the chamber 2. It is also within the scope of the invention to envisage an additional absorbing filter located freely or fixed in the compartment 11. In use, the blood contacts the filter 61, which is typically but not exclusively manufactured from cellulose or polyester fiber and fat particles adhere to the filter 61. This filter 61 further increases the separation of fat and blood already occurring due to flotation of fat to the surface of the stored blood.

Figures 7, 8:
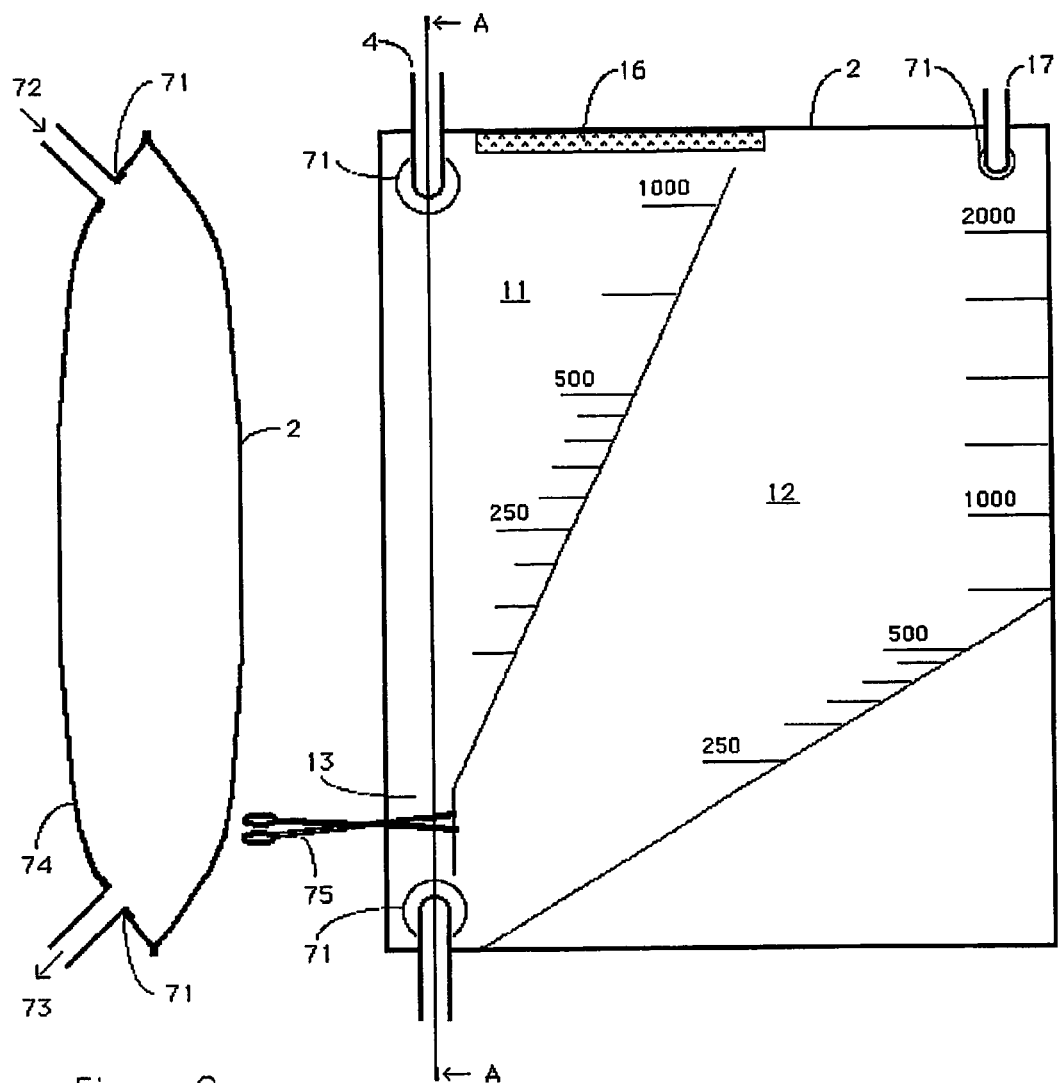
FIG. 7 is an elevation view of a third embodiment of chamber.
FIG. 8 is a side section view of the chamber of FIG. 7 taken along A-A.
Figure 10:
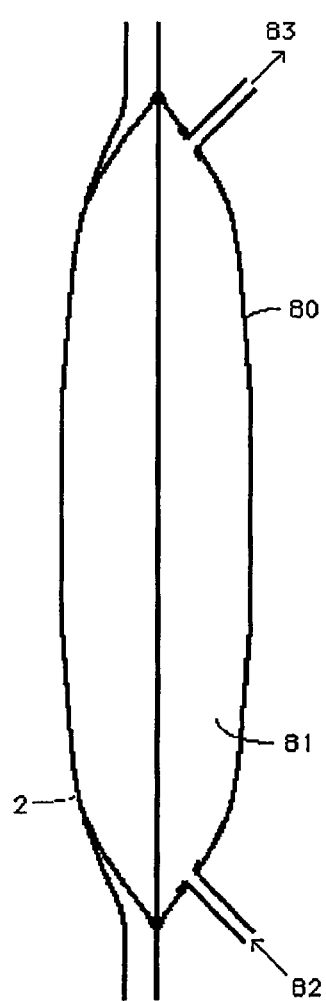
FIG. 10 is a side section view of the apparatus of FIG. 9 taken along A-A.
Figure 9:
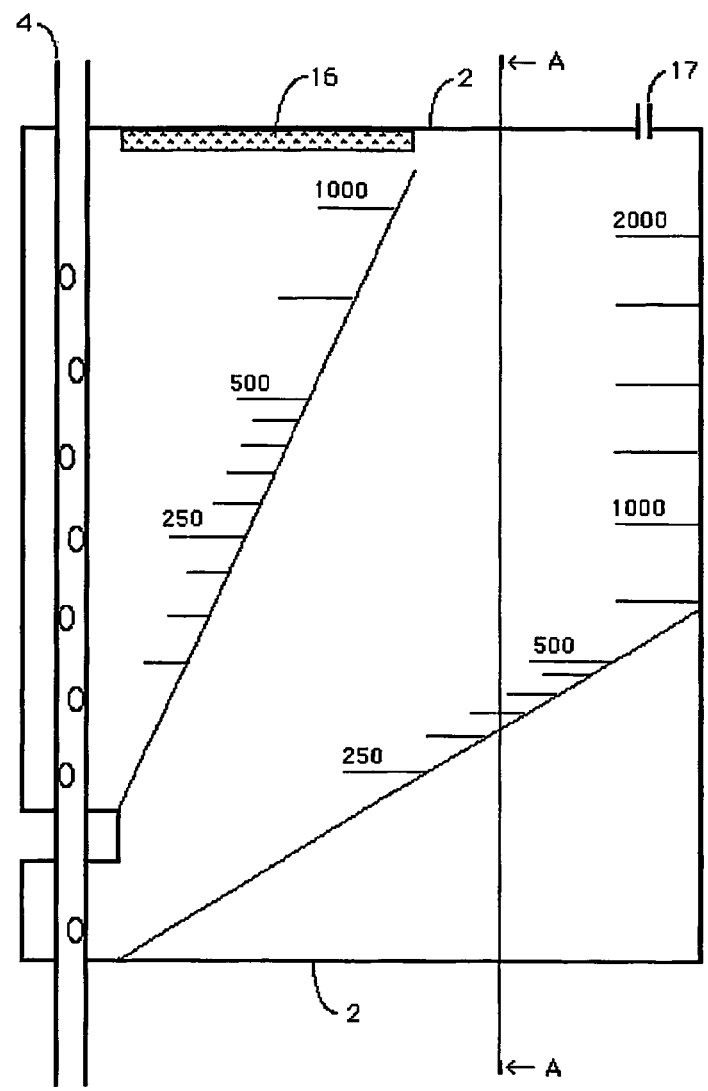
FIG. 9 is an elevation view of an apparatus for separating fat from blood.

FIGS. 7 and 8 show a third embodiment of chamber 2 having specially formed attachments 71 integrated into a side 74 of the chamber 2 for inlet pipe 72 and outlet pipe 73. A similar attachment 71 is used for the air escape valve 17. This construction removes the need for a pipe 4 extending within the chamber 2. A clamp 75 is mounted directly onto the chamber 2 on or about channel 13 in order to prevent blood from flowing between compartments 11 and 12. It will of course be appreciated that filters of the type described in relation to FIGS. 2 to 6 may be incorporated into the chamber 2 of this embodiment. FIGS. 9 and 10 show the chamber 2 of FIG. 1 incorporating a heat exchanger 80. In particular, FIG. 10 shows a heat exchanger 80 having a heat exchange chamber 81 fixed onto one side, of the chamber 2. The heat exchange chamber 81 has an inlet 82 and an outlet 83 and provides a pathway for a flow, preferably although not exclusively a reverse-flow (relative to the direction of flow of blood), cooling or heating medium which can be pumped through the heat exchange chamber 81. In use, the cooling medium lowers the temperature of the blood towards approximately 5°-10° C. At lowered temperatures, fat in the liquid form contained in the blood solidifies or has a higher viscosity, and is much easier to remove from the blood by contact with absorbing filters 42, 61 as described above. Alternatively, the blood temperature is maintained at 37° C. or increased towards approximately 40° C. in order to lower the viscosity of fat in liquid form which facilitates its separation from the blood medium. In this configuration, the medium passing through the heat exchange chamber 81 has a temperature to prevent cooling and may heat the blood above the 37° C. body temperature. FIGS. 11 and 12 show a different construction of heat exchanger 90 which is provided by a coil 92 fixed to one side of the chamber 2. The coil 92 has an inlet 93 and an outlet 94 which, in combination with the coil 92, provide a pathway for the temperature-controlling medium.

Figures 13, 14:
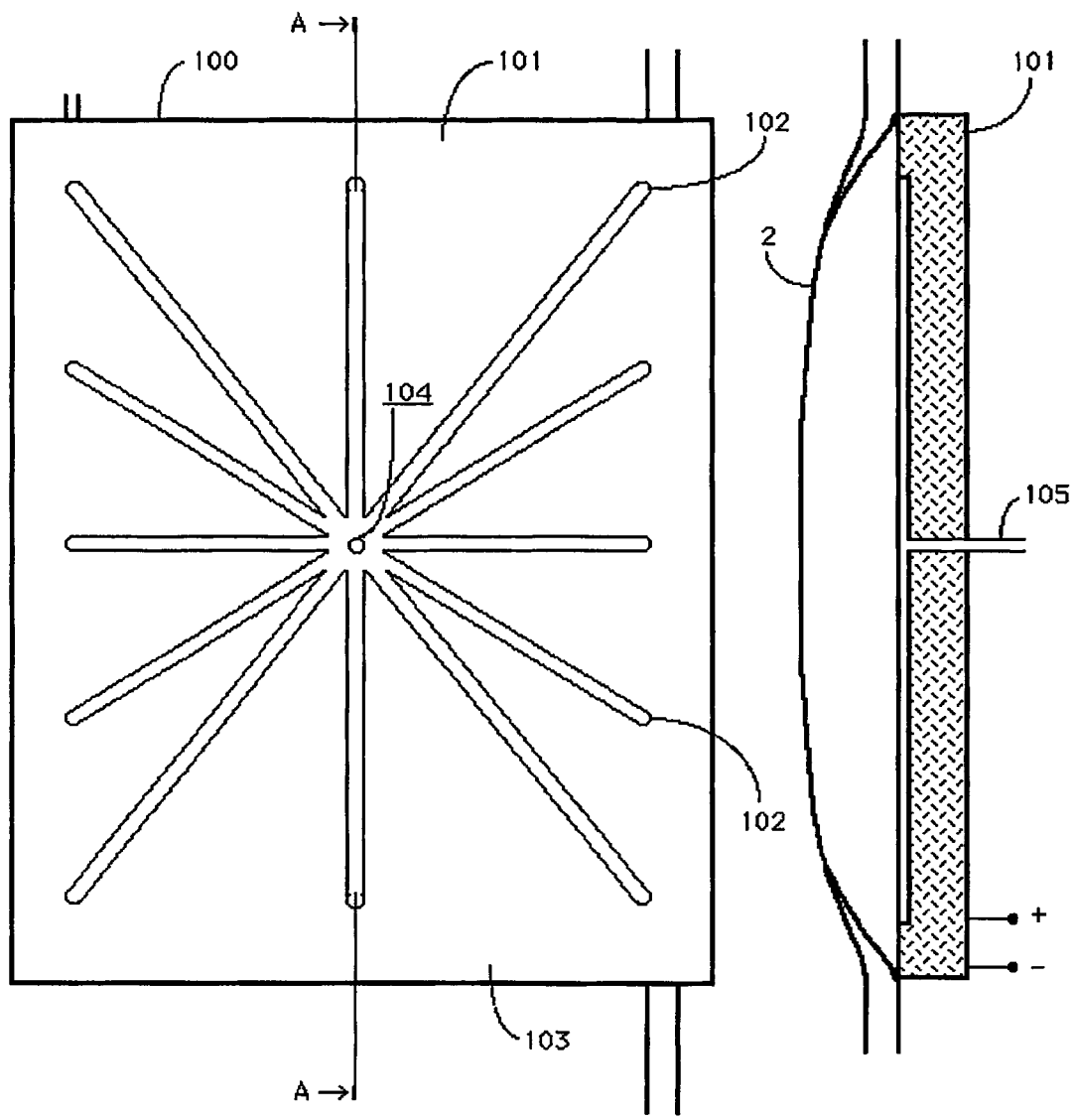
FIG. 13 is an elevation view of a third embodiment of apparatus.
FIG. 14 is a side section elevation view of the apparatus of FIG. 13 taken along A-A.

FIG. 13 and FIG. 14 show an alternative construction of heat exchanger 100 provided by a piezoelectric element 101 mounted on one side of the chamber 2. In this embodiment, the piezoelectric element 101 has a number of recesses 102 on one face 103. The recesses 102 extend from and are spaced angularly around a central point 104 which defines an opening into a bore 105. Alternatively, the bore 105 may be located anywhere along any of the recesses 102. The bore 105 extends through the piezoelectric element 101 and is connected to a vacuum pump (not shown). Alternatively, the bore 105 may extend and connect to the vacuum pump from other locations of the piezoelectric element 101. The piezoelectric element 101 is placed in contact with the chamber 2 and the vacuum pump generates a vacuum resulting in the chamber 2 and piezoelectric element 101 adhering to one another. The piezoelectric element 101 induces cooling of the blood flowing through the chamber 2 via an electrical circuit. A piezoelectric element 101 can be provided on both sides of the chamber 2.

Figure 15:
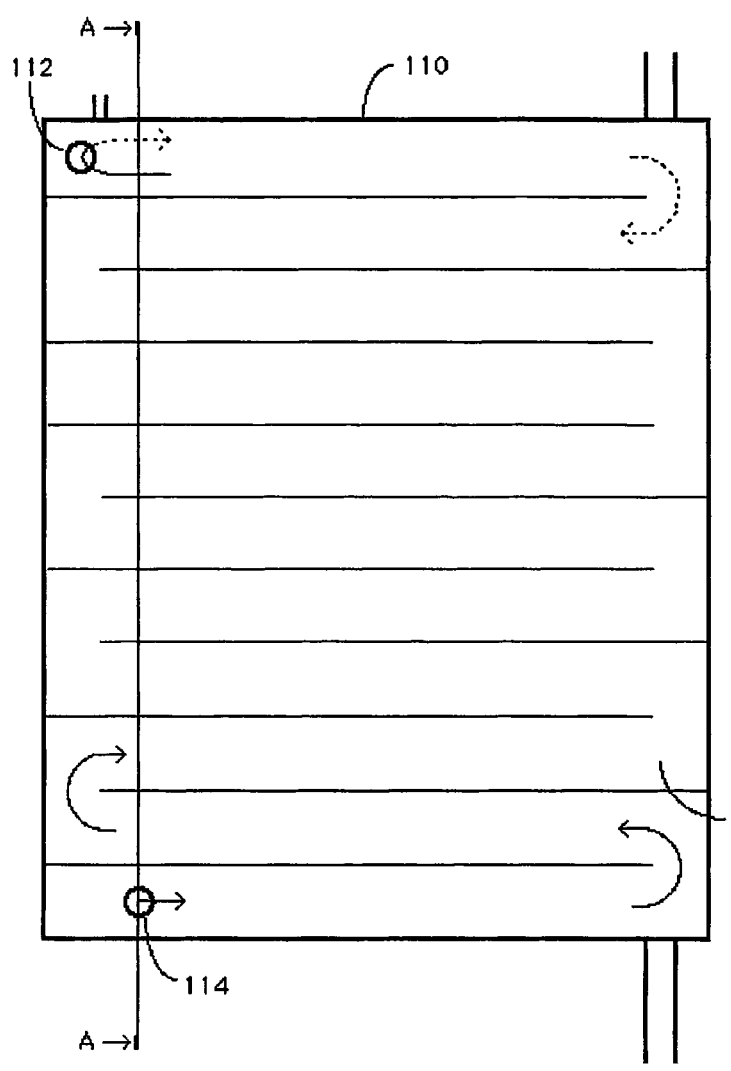
FIG. 15 is an elevation view of a fourth embodiment of apparatus.
Figure 16:
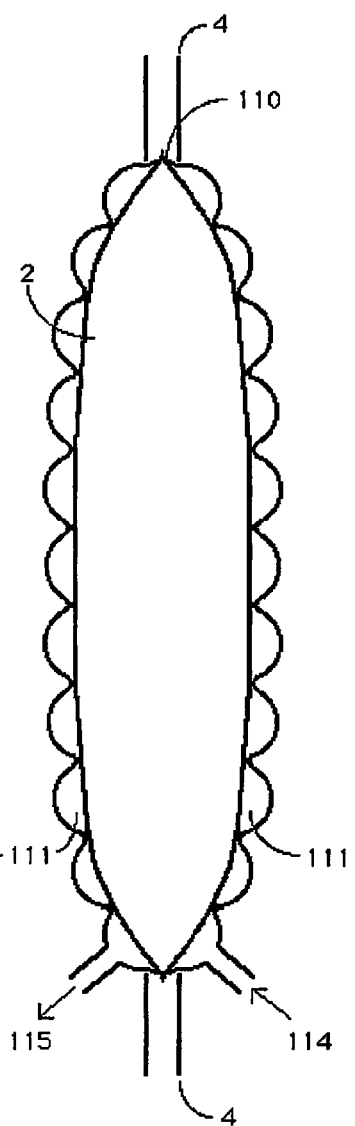
FIG. 16 is a side section elevation view of the apparatus of FIG. 15 taken along A-A.
Figures 17, 18:
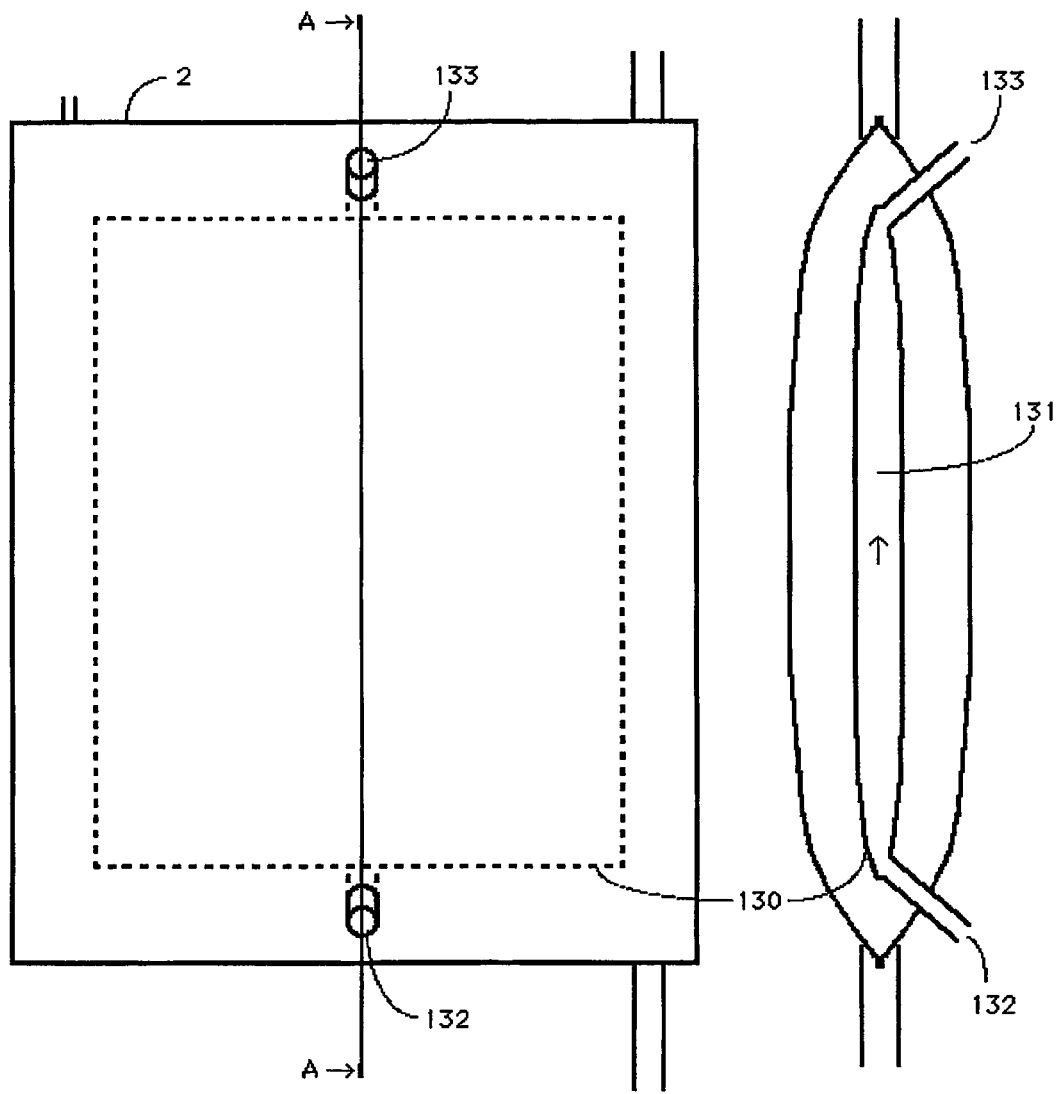
FIG. 17 is an elevation view of a fifth embodiment of apparatus.
FIG. 18 is a side section elevation view of the apparatus of FIG. 17 taken along A-A.

FIGS. 15 and 16 show another configuration of heat exchanger 110 provided by a double-sided coil 111. The double-sided coil 111 is connected via a port 112 allowing the cooling/heating medium to flow through the coil 111 on both sides of the chamber 2. The cooling/heating medium flows in through inlet 114 and up along one side of the coil 111. The medium passes through port 112 and flows down along the opposite side of the chamber 2 and out through outlet 115. It is also possible to provide two separate coils 111, one on each side of the chamber 2. FIGS. 17 and 18 illustrate another embodiment of heat exchanger 130. In this embodiment a heat exchange chamber 131 having an inlet 132 and an outlet 133 is located within the chamber 2. In use, the medium flows into the heat exchange chamber 131 through inlet 132 and is pumped up through the heat exchange chamber 131 contra to the flow of blood or in the same direction.

Figure 19:
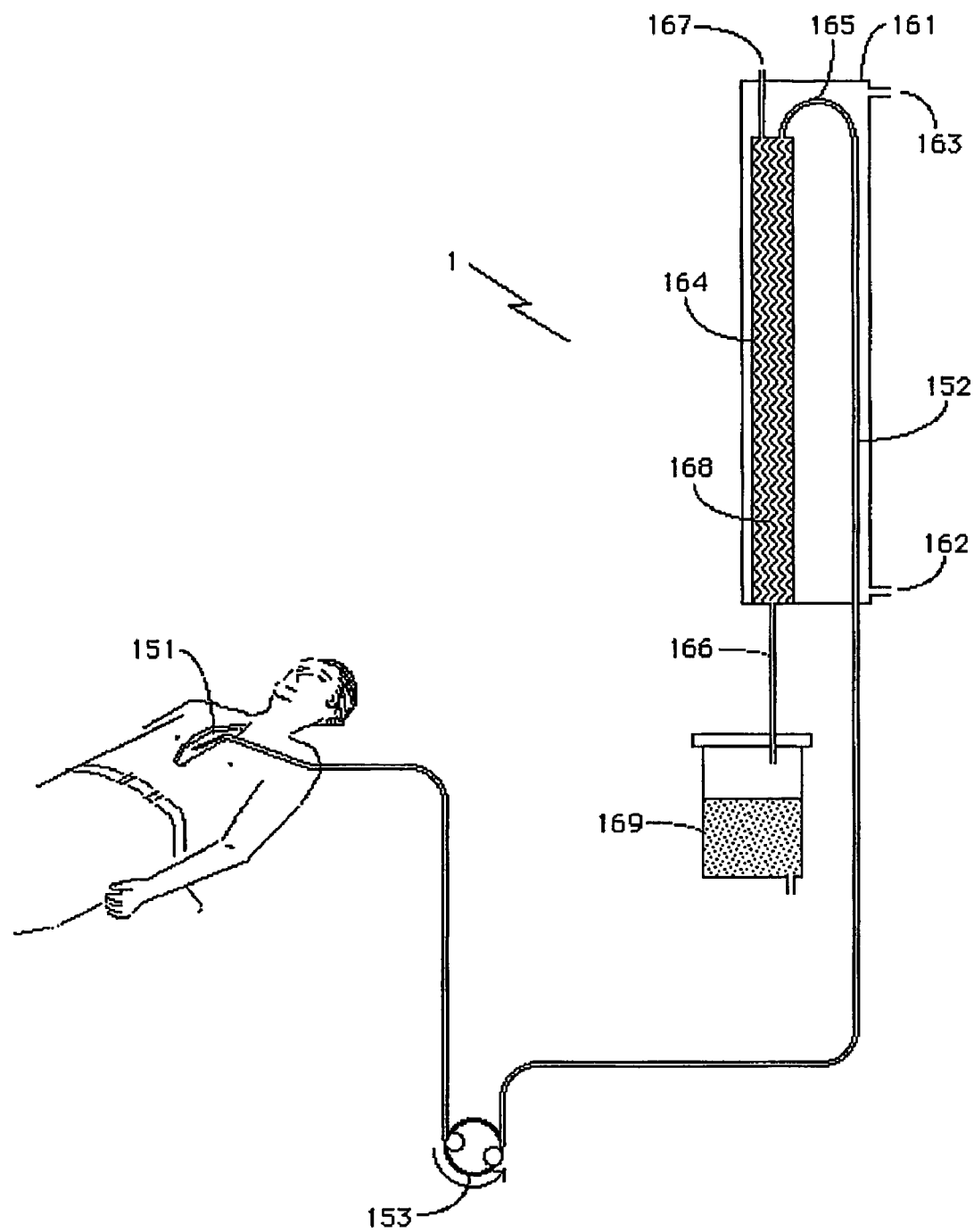
FIG. 19 is a schematic view of a sixth embodiment of apparatus for separating fat from blood.

FIG. 19 illustrates an apparatus 1 having a heat exchanger 161 having an inlet 162 and an outlet 163 providing a flow path for a medium into, through and out of the heat exchanger 161. Within the heat exchanger 161 is a separation chamber 164 having a blood inlet pipe 165 and a blood outlet pipe 166. The separation chamber 164 also includes an air escape valve 167 and has an absorbing filter 168 housed within the chamber 164. The blood outlet pipe 166 flows to a venous reservoir 169, the venous reservoir 169 being a part of commercially available heart and lung machines used for cardiac surgery. Alternatively, the blood with reduced fat may also be allowed to drain directly into the body of the patient (not shown). In use, pericardial blood is pumped by a standard pump 153 from surgery site 151 to the separation chamber 164 via the blood inlet pipe 165. It will of course be appreciated that blood could be aspirated by the standard pump 153 or a vacuum source (not shown) through the separation chamber 164 for which mode of action the air escape valve 167 is omitted. A portion 152 of the blood inlet pipe 165 is contained within the heat exchanger 161 and blood flowing through this portion 152 is subject to cooling prior to entering the chamber 164 by the cooling medium flowing through the heat exchanger 161. The cooled blood has a temperature towards approximately 5°-10° C. as it enters the chamber 164. At this temperature the fat contained within the blood has solidified, or reached a level of high viscosity, and is absorbed by the filter 168, which preferably but not exclusively is formed from cellulose or polyester fiber. The fat-reduced blood returns to the venous reservoir 169. In this embodiment, blood can flow continuously from the surgery site 151 through the apparatus without the need for clamps or other flow restrictors. The chamber 164 is produced from a pliable transparent plastic material, although they are not limited to this particular material. A chamber 164 manufactured from a rigid material is also within the scope of the invention. The heat exchanger 161 could have features similar to that described in any of the previous FIGS. 9 to 18.

Figure 20:
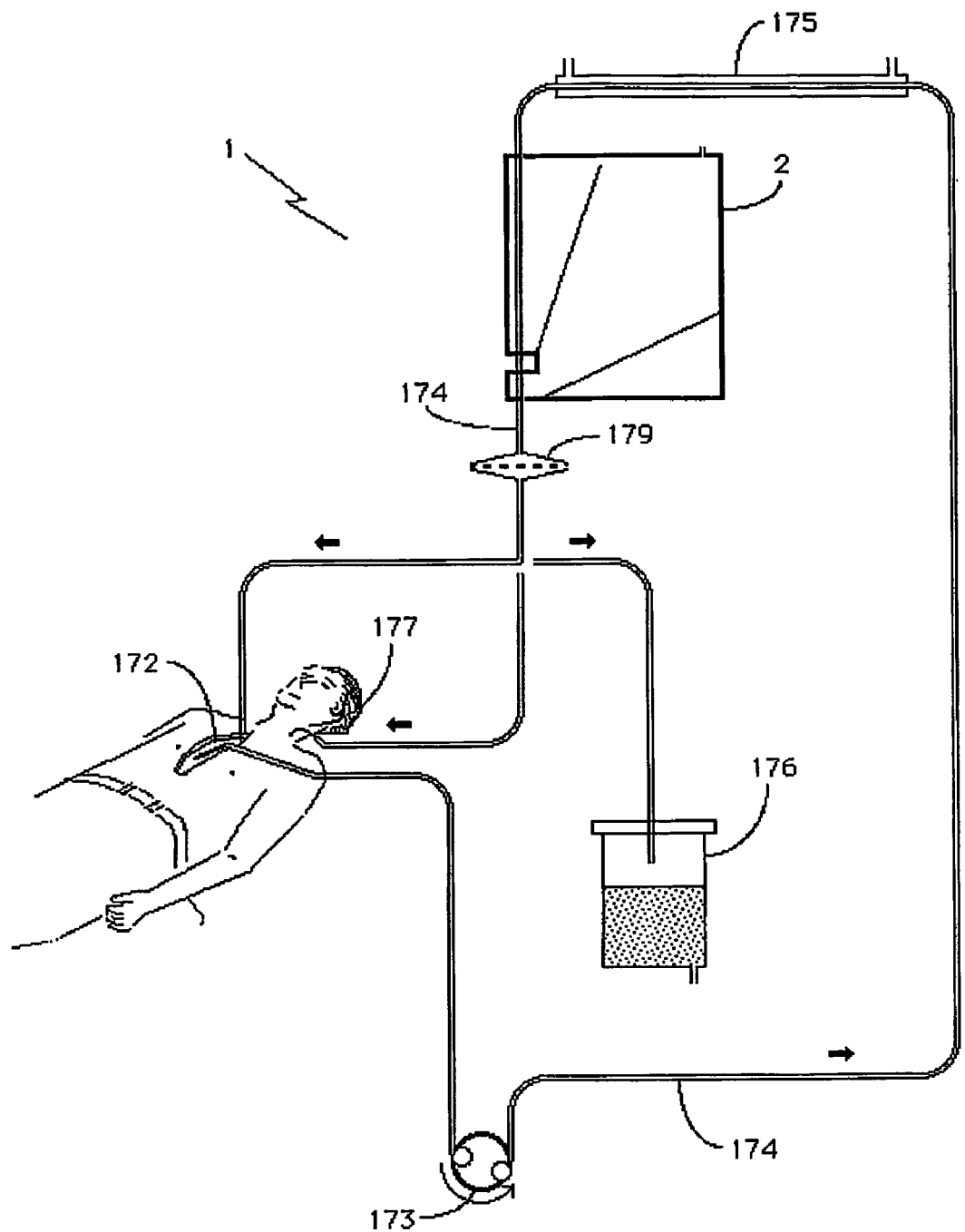
FIG. 20 is a schematic view of a seventh embodiment of apparatus for separating fat from blood.

FIG. 20 shows an apparatus 1 having a pump 173 mounted on a pipe 174 between the surgery site 172 and a heat exchanger 175. The heat exchanger 175 is mounted on a portion of the pipe 174 leading into chamber 2. The chamber 2 in this embodiment is similar in construction and function to the chamber 2 described in FIG. 1. A commercially available filter 179 for through flow of blood such as (PALL Leuko-Guard RS®, PALL Medical, Portsmouth, England) is provided on a section of the pipe 174 leading away from the chamber 2. The pipe 174 is then connected to a venous reservoir 176 or is connected directly back to the body of the patient 177. In use, blood is pumped from the surgery site 172 by a standard pump 173 to the heat exchanger 175 via the pipe 174. The heat exchanger 175 is used to reduce the temperature of the blood towards approximately 5°-10° C. The chamber 2 includes a number of absorbing filters (not shown) which are preferably, but not exclusively manufactured from cellulose or polyester fiber. Fat in the pericardial suction blood solidifies or reaches a level of high viscosity at reduced temperatures and is absorbed by the filters. In addition, the blood and fat can be separated further in the chamber 2 as described in the in use description of FIG. 1. The commercial filter 179 removes any fat remaining in the blood after it passes through the chamber 2. The blood is then alternatively redirected to the venous reservoir 176 or back to the patient's body 177.

Figure 21:
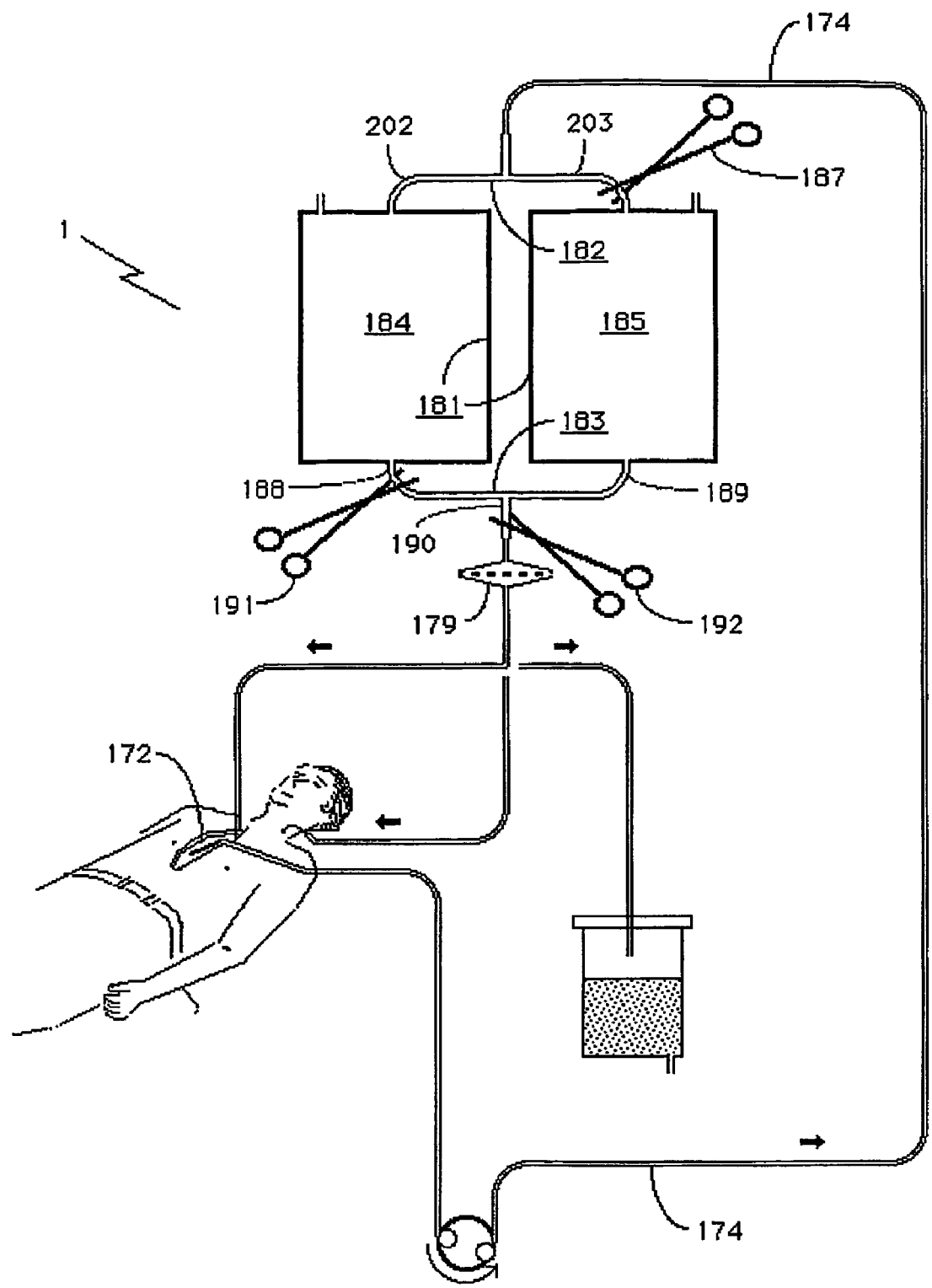
FIG. 21 is an eight embodiment of apparatus.

Referring to FIG. 21 there is shown a chamber 181 comprising compartments 184 and 185 as separate units connected by pipes 182 and 183. It will of course be appreciated that a heat exchanger as previously discussed could also be applied to the apparatus 1 of this embodiment. The pipe 174 from the surgery site 172 branches into two separate pipes 202, 203 which enter a chamber 184 and 185 respectively. A clamp 187 blocks the pipe 203 entering chamber 185. Outlet pipes 188, 189 extend from the base of the compartments 184 and 185 respectively and these pipes merge together to form a single pipe 190. A second clamp 191 blocks the pipe 188 emerging from compartment 184 and a third clamp 192 blocks the pipe 190. In use, blood flows unimpeded into compartment 184 until it reaches clamp 191. The fat in the blood collecting in compartment 184 starts to float towards the surface of the blood. When the compartment 184 has a predetermined amount of blood contained therein, lamp 191 is opened and the blood flows through the outlet pipe 188 and up into the compartment 185. The fat which has collected adjacent the surface of the blood remains in the compartment 184. The clamp 191 is closed when the desired amount of blood has flown into the compartment 185. This blood is allowed to settle again in the compartment 185 in order to allow additional fat to float to the surface of the blood. After a predetermined period, clamp 192 is released and all the blood except the blood containing the separated fat is allowed to flow out of the compartment 185. This blood flows through filter 179 removing still further fat. It will of course be appreciated that filters can be located in both or either of the compartments 184 and 185. In an alternative mode of operation, the two compartments 184 and 185 can be used separately. In use, blood flows unimpeded into compartment 184 until it reaches clamp 191. When the compartment 184 has a predetermined amount of blood contained therein, clamp 187 is opened and moved to instead occlude inlet pipe 202. Additional blood now enters the opened inlet tube 203 and container 185. The fat in the blood collected in compartment 184 starts to float towards the surface of the blood without interference from turbulence of incoming blood. After a predetermined time the lower fraction of blood in container 184 is emptied by first occluding the outlet pipe 189, by moving the clamp 192 to its new location 189, and opening the outlet pipe 188 by removing clamp 191. The top fraction of blood in container 184, holding a concentrated amount of fat, is prevented from reaching the patient by re-occluding outlet pipe 188 using clamp 191. The same procedure is carried out with compartment 185 after filling with further incoming blood being re-directed to again fill compartment 184.

Figure 22:
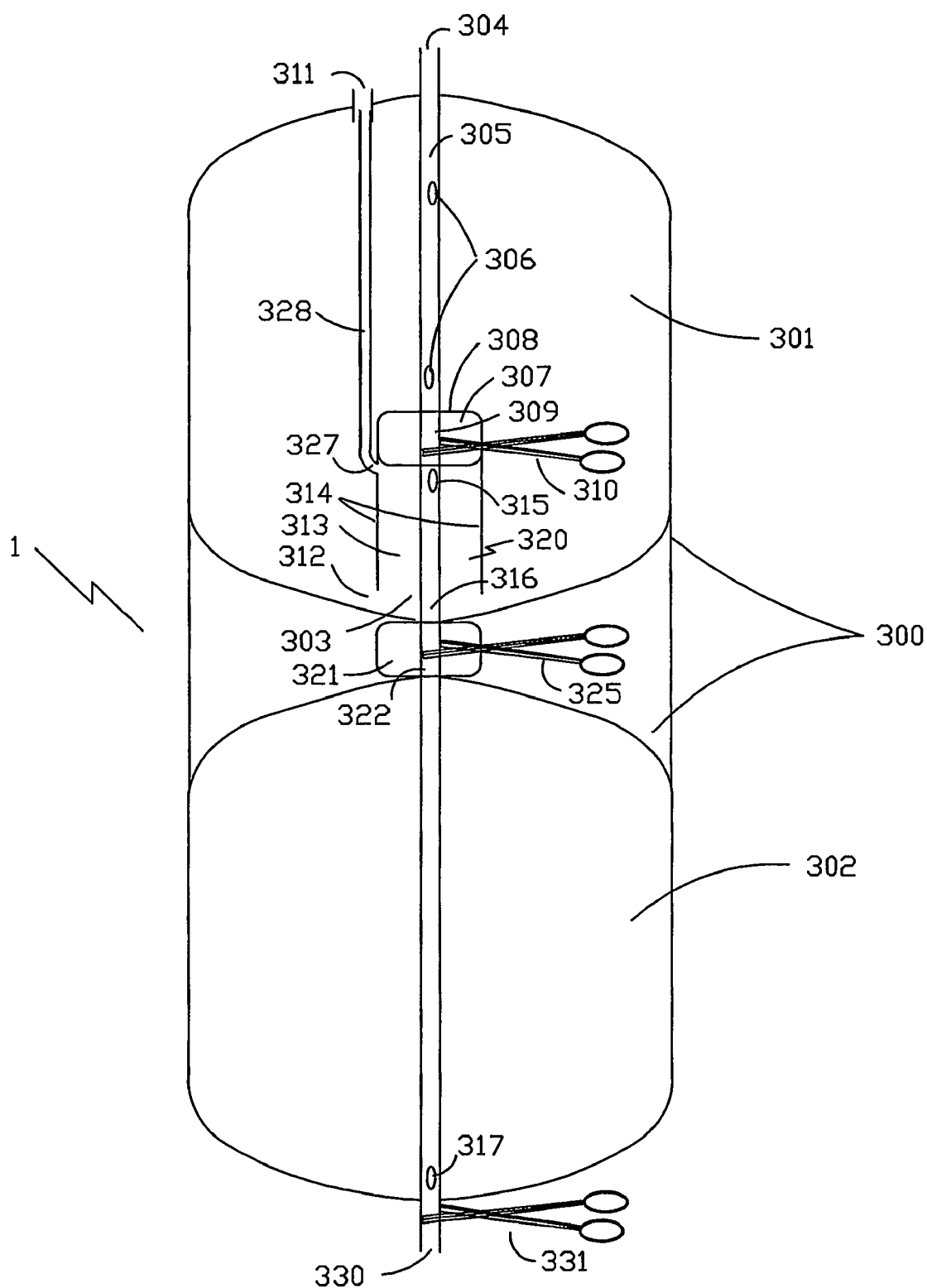
FIG. 22 is a ninth embodiment of apparatus.

Referring to the drawings and finally to FIG. 22 there is shown an apparatus 1 having a chamber 300 comprising compartments 301 and 302 and with an interconnecting conduit 303. The chamber 300 is substantially as described in FIG. 1 with reference to chamber 2 but with a spatial arrangement of compartment 301 being above compartment 302. An inlet 304 directs blood via pipe 305 to collect in compartment 301 via perforations 306 identical to what is described for pipe 4, compartment 11, and perforations 201 in FIG. 1. The pipe 305 is here illustrated to have essentially a central location within chamber 300 but can be located along the edge of chamber 300 similar to what is described for pipe 4 of chamber 2 in FIG. 1. The chamber 300 has an opening 307 positioned within the space of compartment 301 created by an encircling welded seam 308 exposing a portion 309 of the pipe 305. A first sealing clamp 310 is mounted on the exposed portion 309 of the pipe 305 to block the pipe 305 in order for blood to collect in compartment 301. Air that collects in compartment 301 together with blood pumped from the patient's wound escapes from compartment 301 via a valve opening 311 that is positioned essentially along the top edge of compartment 301, similar to what is described for valve 17 in FIG. 1. In the case of excess of blood in compartment 301, due to accidental filling by the perfusionist, blood escapes through the named valve 311. The valve 311 could be connected by a separate pipe to the venous reservoir (not shown). The compartment 301 is in connection with compartment 302 via the conduit 303. The conduit 303 comprises a channel 312 at the bottom of compartment 301, an entrapped space 313 of compartment 301 created by two welded seams 314 that connects with the welded seam 308, perforation 315 of pipe 305, an extension 316 of pipe 305 into compartment 302, and perforation 317 of pipe 305. The spatial arrangement of the details 312, 313, 315, and 316 of conduit 303 create together a water-lock mechanism 320. The water-lock mechanism 320 is symmetrically arranged on both sides of the pipe 305 but can also be single-sided in the case the pipe 305 is located along the edge of the chamber 300, similar to what is described in FIG. 1. It is of course appreciated that the arrangement of details within the water-lock mechanism 320 is not limited to the described design. The conduit 303 has an opening 321, similar to 307, exposing a section 322 of the pipe 316. A second sealing clamp 325 is mounted on the exposed section 322 of the pipe 316 to open and close the conduit 303. Located at the top of the entrapped space 313 is a venting port 327 consisting of a pipe 328 inside compartment 301 in connection with the top of chamber 300. The pipe 328 could connect with the valve opening 311. It is of course appreciated that the port 327 and venting pipe 328 can have a path outside compartment 301. The venting port 327 of conduit 303 prevents a negative barometric pressure to build up within the water-lock mechanism 320 to prevent a portion of the blood that has accumulated in compartment 301 to fill over to compartment 302 when the sealing clamp 325 is released. Fat collects at the top surface of blood in compartment 301 and remains in compartment 301 together with the top portion of blood that is prevented to flow over into compartment 302. The flow rate by which fat-reduced blood fills over from compartment 301 to compartment 302 is controlled by the flow resistance of conduit 303, in particular but not limited to a narrowing within channel 312. A typical drainage time is about 30 seconds but can set to other time duration depending on use of the apparatus 1. The compartment 302 comprises an extension 316 of pipe 305 with one or more perforations 317, and pipe 305 emerges at the bottom of compartment 302 to form an outlet 330. A third sealing clamp 331 is mounted on the pipe 305 at outlet 330 of compartment 302 to control drainage of blood from the chamber 300 into the venous reservoir (not shown) or back into the patient's body. This chamber 300 is also suitable for allowing through flow of blood by removing all the clamps 310, 325, 331, if high volume bleeding occurs at the surgery site. It is well appreciated within the scope of the invention that the design of compartment 302 can be similar to what is described for compartment 301 comprising a second water-lock mechanism identical to the water-lock 320. The second water lock prevents the last portion of blood in compartment 302, containing a concentrated amount of fat that has accumulated at the top surface of blood, to reach the patient's body. It is also understood that additional compartments, identical to 301 and 302, can be connected in series to form a multi-compartment fat-separation chamber. It will further be appreciated that a fat-absorbing filter of the type described in relation to FIGS. 2 to 6 may be incorporated into the chamber 300 of this embodiment, that a heat exchanger as previously discussed could also be applied to the apparatus 1 of this embodiment, and that pipe connections 71 of FIGS. 7 and 8 could be used within this embodiment. The chamber 300 and pipe 305 described in this embodiment are produced from a pliable transparent plastic material, although they are not limited to this particular material. A chamber 300 manufactured from a rigid material is also within the scope of the invention.

It will of course be appreciated that the clamps described are not limited to manual actuation and could be operated mechanically, electrically, pneumatically or hydraulically.

It will of course be appreciated that the invention is not limited to the detailed description of the specific embodiments, which are given by way of example only, and that various alterations and modifications may be made to the embodiments without departing from the scope of the invention as defined in the appended claims.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. An apparatus for reducing fat in blood comprising:
a chamber, said chamber having an inlet and an outlet and comprising:
a first compartment for receiving blood via the inlet;
a second compartment in fluid communication with the first compartment via a channel that connects a base of the first compartment with the second compartment, the second compartment defining the outlet; and
means for preventing a remaining portion of the blood in the first compartment from flowing out of the first compartment when blood flows from the first compartment into the second compartment during use,
wherein said first and second compartments are made of a pliable plastic material,
wherein the apparatus is arranged to be integrated in a cardiopulmonary bypass circuit and for reducing fat in pericardial blood, and the inlet is arranged to receive pericardial suction blood pumped from a surgery site, and
wherein a blood pipe passes through the inlet, the chamber and the outlet, and a portion of the blood pipe within the chamber has perforations formed therein.

2. The apparatus as claimed in claim 1, wherein the second compartment is located vertically below the first compartment.

3. The apparatus as claimed in claim 1, wherein the means for preventing the remaining portion of the blood in the first compartment from flowing out of the first compartment when blood flows from the first compartment into the second compartment during use comprises a water-lock mechanism, and during use a portion of blood collected in the first compartment is prevented from leaving the first compartment when the channel is opened to let blood flow into the second compartment.

4. The apparatus as claimed in claim 3, wherein the water-lock mechanism comprises an entrapped space formed around an opening to the channel.

5. The apparatus as claimed in claim 4, wherein the water-lock mechanism further comprises a venting port.

6. The apparatus as claimed in claim 1, wherein the channel includes a geometric narrowing, whereby the volumetric flow rate of blood flowing into the second compartment from the first compartment is controlled during use.

7. The apparatus as claimed in claim 1, wherein the channel is releasably sealable by a sealing device.

8. The apparatus as claimed in claim 1, wherein said channel that connects the base of the first compartment with the second compartment is formed between perforations in said blood pipe.

9. The apparatus as claimed in claim 1, wherein said blood pipe has an essentially central location within the chamber.

10. The apparatus as claimed in claim 1, wherein a fat-absorb filter is located in at least one of the first and second compartments.

11. The apparatus as claimed in claim 10, wherein the fat-absorb filter is manufactured from cellulose or polyester fiber.

12. The apparatus of claim 1, further comprising a vent opening arranged at the top of the first compartment, said vent opening allowing air which is pumped together with blood and received through said inlet to escape from the first compartment.

13. The apparatus of claim 1, further comprising a direct communication between said inlet and said outlet, said direct communication being openable to by-pass said waterlock mechanism.

14. The apparatus of claim 1, wherein the channel connecting the base of the first compartment with the second compartment and the means for preventing a remaining portion of the blood in the first compartment to flow out of the first compartment are also made of a pliable material.

15. The apparatus of claim 1, wherein the first and second compartments are formed by one chamber divided into said first and second compartments by a welded seam.

16. An apparatus for reducing fat in blood comprising:
a chamber having an inlet and an outlet and comprising:
a first compartment for receiving blood via the inlet; and
a second compartment in fluid communication with the first compartment via a channel that connects a base of the first compartment with the second compartment, the second compartment defining the outlet; and
a water-lock mechanism for preventing a remaining portion of the blood in the first compartment from flowing out of the first compartment when the channel is opened to let blood flow into the second compartment during use, wherein said first and second compartments are made of a pliable plastic material, wherein the apparatus is arranged to be integrated in a cardiopulmonary bypass circuit and for reducing fat in pericardial blood, and the inlet is arranged to receive pericardial suction blood pumped from a surgery site, and wherein a blood pipe passes through the inlet, the chamber and the outlet, and a portion of the blood pipe within the chamber has perforations defined therein.

17. The apparatus as claimed in claim 16, wherein the second compartment is located vertically below the first compartment.

18. The apparatus as claimed in claim 16, wherein the channel connects the base of the first compartment with a top of the second compartment.

19. The apparatus as claimed in claim 16, wherein the water-lock mechanism comprises an entrapped space formed around an opening to the channel.

20. The apparatus as claimed in claim 19, wherein the water-lock mechanism further comprises a venting port.

21. The apparatus as claimed in claim 16, wherein the channel is releasably sealable by sealing device.

22. The apparatus as claimed in claim 16, wherein said channel that connects the base of the first compartment with the second compartment is formed between perforations in said blood pipe.

23. The apparatus as claimed in claim 16, wherein said blood pipe has an essentially central location within the chamber.

24. The apparatus of claim 16, further comprising a vent opening arranged at the top of the first compartment, said vent opening allowing air which is pumped together with blood and received through said inlet to escape from the first compartment.

25. The apparatus of claim 16, further comprising a direct communication between said inlet and said outlet, said direct communication being openable to by-pass said waterlock mechanism.

26. The apparatus of claim 16, wherein the channel connecting the base of the first compartment with the second compartment and the water-lock mechanism are also made of a pliable material.

27. The apparatus of claim 16, wherein the first and second compartments are formed by one chamber divided into said first and second compartments by a welded seam.

28. An apparatus for reducing fat in blood comprising:
a chamber, said chamber having an inlet and an outlet and comprising:
a first compartment for receiving blood via the inlet;
a second compartment in fluid communication with the first compartment via a channel which connects the base of the first compartment with the second compartment, the second compartment defining the outlet; and
means for preventing a remaining portion of the blood in the first compartment to flow out of the first compartment when blood flows from the first compartment into the second compartment during use;

wherein said first and second compartments are made of a pliable plastic material, the pliability of the pliable plastic material enabling rolling together of said first and second compartments, and wherein a blood pipe passes through the inlet, the chamber and the outlet, and a portion of the blood pipe within the chamber has perforations defined therein.

29. The apparatus of claim 28, further comprising a vent opening arranged at the top of the first compartment, said vent opening allowing air which is pumped together with blood and received through said inlet to escape from the first compartment.

30. The apparatus of claim 28, further comprising a direct communication between said inlet and said outlet, said direct communication being openable to by-pass said waterlock mechanism.

31. The apparatus of claim 28, wherein the channel connecting the base of the first compartment with the second compartment and the means for preventing a remaining portion of the blood in the first compartment to flow out of the first compartment are also made of a pliable material.

32. The apparatus of claim 28, wherein the first and second compartments are formed by one chamber divided into said first and second compartments by a welded seam.

33. An apparatus for reducing fat in blood comprising:
a chamber having an inlet and an outlet and comprising:
a first compartment for receiving blood via the inlet;
a second compartment in fluid communication with the first compartment via a channel that connects the base of the first compartment with the second compartment, the second compartment defining the outlet; and
a water-lock mechanism for preventing a remaining portion of the blood in the first compartment from flowing out of the first compartment when the channel is opened to let blood flow from into the second compartment during use;

wherein said first and second compartments are made of a pliable plastic material, the pliability of the pliable plastic material enabling rolling together of said first and second compartments, and wherein a blood pipe passes through the inlet, the chamber and the outlet, and a portion of the blood pipe within the chamber has perforations defined therein.

34. The apparatus of claim 33, further comprising a vent opening arranged at the top of the first compartment, said vent opening allowing air which is pumped together with blood and received through said inlet to escape from the first compartment.

35. The apparatus of claim 33, further comprising a direct communication between said inlet and said outlet, said direct communication being openable to by-pass said waterlock mechanism.

36. The apparatus of claim 33, wherein the channel connecting the base of the first compartment with the second compartment and the water-lock mechanism are also made of a pliable material.

37. The apparatus of claim 33, wherein the first and second compartments are formed by one chamber divided into said first and second compartments by a welded seam.

* * * * *